(12) United States Patent
Aoki et al.

(10) Patent No.: US 9,472,829 B2
(45) Date of Patent: Oct. 18, 2016

(54) METHOD FOR STABILIZING LIPF$_6$, ELECTROLYTE SOLUTION FOR NONAQUEOUS SECONDARY BATTERIES HAVING EXCELLENT THERMAL STABILITY, AND NONAQUEOUS SECONDARY BATTERY HAVING EXCELLENT THERMAL STABILITY

(71) Applicant: TOSOH F-TECH, INC., Shunan-shi (JP)

(72) Inventors: Masahiro Aoki, Shunan (JP); Hideyuki Mimura, Shunan (JP); Hisao Eguchi, Shunan (JP)

(73) Assignee: TOSOH F-TECH, INC., Shunan-shi (JP)

( * ) Notice: Subject to any disclaimer, the term of this patent is extended or adjusted under 35 U.S.C. 154(b) by 142 days.

(21) Appl. No.: 14/406,884

(22) PCT Filed: Jun. 13, 2013

(86) PCT No.: PCT/JP2013/003736
§ 371 (c)(1),
(2) Date: Dec. 10, 2014

(87) PCT Pub. No.: WO2013/187073
PCT Pub. Date: Dec. 19, 2013

(65) Prior Publication Data
US 2015/0140445 A1 May 21, 2015

(30) Foreign Application Priority Data

Jun. 15, 2012 (JP) .................. 2012-135520
Nov. 5, 2012 (JP) .................. 2012-243280

(51) Int. Cl.
*H01M 10/0567* (2010.01)
*H01M 10/052* (2010.01)
(Continued)

(52) U.S. Cl.
CPC .......... *H01M 10/0567* (2013.01); *C07F 9/091* (2013.01); *C07F 9/11* (2013.01);
(Continued)

(58) Field of Classification Search
CPC .. H01M 10/0567; H01G 11/58; C07F 9/091; C07F 9/11; C07F 9/1411; C07F 9/224; C07F 9/2458; C07F 9/2462; C07F 9/2466; C07F 9/247; C07F 9/650958; C07F 9/6533; C07F 9/6544; C07F 9/24
See application file for complete search history.

(56) References Cited

U.S. PATENT DOCUMENTS

| 6,939,647 | B1 | 9/2005 | Jow et al. |
| 2012/0100436 | A1 | 4/2012 | Inoue et al. |
| 2013/0337317 | A1* | 12/2013 | Shima ............ H01M 10/052 429/188 |

FOREIGN PATENT DOCUMENTS

| JP | 2002-356491 A | 12/2002 |
| JP | 2003-034692 A | 2/2003 |

(Continued)

OTHER PUBLICATIONS

International Search Report issued Aug. 20, 2013 in PCT/JP2013/003736 Filed Jun. 13, 2013.

*Primary Examiner* — Ula C Ruddock
*Assistant Examiner* — Thomas Parsons
(74) *Attorney, Agent, or Firm* — Oblon, McClelland, Maier & Neustadt, L.L.P.

(57) ABSTRACT

A method for stabilizing a solution that contains LiPF$_6$ by increasing thermal stability of LiPF$_6$ without changing the structure thereof; an electrolyte solution for nonaqueous secondary batteries, which has increased thermal stability; and a nonaqueous secondary battery which has increased thermal stability. The solution containing LiPF$_6$ contains a phosphoric acid ester amide in such an amount that the molar ratio of the phosphoric acid ester amide relative to LiPF$_6$ is 0.001-2.

11 Claims, 1 Drawing Sheet

(51) Int. Cl.
*H01M 10/0568* (2010.01)
*C07F 9/24* (2006.01)
*H01G 11/56* (2013.01)
*C07F 9/6509* (2006.01)
*C07F 9/6533* (2006.01)
*C07F 9/6544* (2006.01)
*C07F 9/09* (2006.01)
*C07F 9/11* (2006.01)
*C07F 9/141* (2006.01)
*C07F 9/22* (2006.01)
*H01G 11/58* (2013.01)
*H01M 10/0569* (2010.01)

(52) U.S. Cl.
CPC ............ *C07F 9/1411* (2013.01); *C07F 9/224* (2013.01); *C07F 9/24* (2013.01); *C07F 9/247* (2013.01); *C07F 9/2458* (2013.01); *C07F 9/2462* (2013.01); *C07F 9/2466* (2013.01); *C07F 9/6533* (2013.01); *C07F 9/6544* (2013.01); *C07F 9/650958* (2013.01); *H01G 11/56* (2013.01); *H01G 11/58* (2013.01); *H01M 10/052* (2013.01); *H01M 10/0568* (2013.01); *H01M 10/0569* (2013.01); *H01M 2300/0025* (2013.01); *H01M 2300/0037* (2013.01); *Y02E 60/122* (2013.01); *Y02E 60/13* (2013.01); *Y02T 10/7011* (2013.01); *Y02T 10/7022* (2013.01)

(56) References Cited

FOREIGN PATENT DOCUMENTS

| | | |
|---|---|---|
| JP | 2007-157399 A | 6/2007 |
| JP | 2011-003498 A | 1/2011 |
| JP | 2011-141974 A | 7/2011 |
| JP | 2012-164441 A | 8/2012 |
| JP | 2012-190791 A | 10/2012 |
| WO | WO 2010/092829 A1 | 8/2010 |
| WO | WO 2010/150508 A1 | 12/2010 |
| WO | WO 2012/115119 A1 | 8/2012 |

* cited by examiner

METHOD FOR STABILIZING LIPF$_6$, ELECTROLYTE SOLUTION FOR NONAQUEOUS SECONDARY BATTERIES HAVING EXCELLENT THERMAL STABILITY, AND NONAQUEOUS SECONDARY BATTERY HAVING EXCELLENT THERMAL STABILITY

TECHNICAL FIELD

The present invention relates to a method for thermally stabilizing LiPF$_6$ in a solution containing LiPF$_6$ that is used for a nonaqueous secondary battery such as a lithium ion secondary battery and a lithium ion capacitor, an electrolyte solution for nonaqueous secondary batteries having excellent thermal stability, and a nonaqueous secondary battery having excellent thermal stability.

BACKGROUND ART

A nonaqueous secondary battery typified by a lithium ion secondary battery has high power density and high energy density, and has been generally used as a power supply for a cell phone, a note-type personal computer, or the like.

In recent years, a large battery has been practically used as a power supply for electric power storage or a power supply for electric automobiles.

Further, various electrochemical capacitors that operate in accordance with a principle similar to that of an electric double layer capacitor have been developed recently. An attention has been paid to an energy storage device combining the electricity accumulation principle of a lithium ion secondary battery and that of an electric double layer capacitor, which is called lithium ion capacitor (Non-Patent Literature 1).

An increase in the size of a battery has been required, and an increase in the useful life of the battery has also been required, since it is assumed that the battery is used under severe conditions at higher temperature especially for use in an electric automobile.

As an electrolyte solution of such a nonaqueous secondary battery, a solution in which an electrolyte is dissolved in a mixed solvent of a cyclic carbonate such as ethylene carbonate and a chain carbonate such as ethylmethyl carbonate is generally used. As a lithium salt that is the electrolyte, LiPF$_6$ is used. This is because LiPF$_6$ has high solubility in the solvent and high ion conductivity at a wide temperature range from low temperature to high temperature, and a side reaction is unlikely to be caused on an electrode due to the wide potential window of LiPF$_6$. However, since LiPF$_6$ does not have sufficient thermal stability, LiPF$_6$ is decomposed by heating or in storage for a long period. Furthermore, an unstable intermediate produced by decomposition of LiPF$_6$ is hydrolyzed by a trace amount of water contained in the solvent and promotes decomposition of the solvent to produce lithium fluoride and hydrogen fluoride. When LiPF$_6$ is decomposed, the ion conductivity of an electrolyte solution containing the decomposed products of LiPF$_6$ decreases. At the same time, the produced lithium fluoride and hydrogen fluoride corrode materials for an electrode and a collector, and a gas is generated by decomposition of the solvent to increase a pressure inside the battery. The battery may be significantly adversely affected (Non-Patent Literatures 2 and 3).

As an electrolyte having higher thermal stability to overcome the disadvantages of LiPF$_6$, LiBF$_4$, LiCF$_3$SO$_3$, LiN(CF$_3$SO$_2$)$_2$, and the like are known. However, a nonaqueous electrolyte solution of LiBF$_4$ or LiCF$_3$SO$_3$ has improved thermal stability as compared with LiPF$_6$, but a problem of decrease in the ion conductivity arises. A nonaqueous electrolyte solution of LiN(CF$_3$SO$_2$)$_2$ does not have sufficient oxidation resistance, and has a problem such as corrosion of aluminum metal that is used for a positive electrode collector.

On the other hand, Patent Literatures 1, 2, and 3 disclose a method for increasing thermal stability and hydrolysis resistance of an electrolyte by using fluoroalkyl phosphate in which fluorine atoms of LiPF$_6$ are partially substituted by a perfluoroalkyl group. However, this prior art also has a problem of decrease in oxidation resistance since fluorine atoms bonded to a phosphorous atom are partially substituted with carbon atoms.

Non-Patent Literatures 4 and 5 and Patent Literatures 4 and 5 propose a specific phosphorous acid ester(tris(2,2,2-trifluoroethyl)phosphite) and hexamethylphosphoramide as an additive that thermally stabilizes LiPF$_6$. However, the phosphorous acid ester and hexamethylphosphoramide herein are not electrochemically stable. Therefore, when a battery containing a phosphorous acid ester or hexamethylphosphoramide is repeatedly charged and discharged at high voltage, decomposition occurs, and the battery performance is insufficient.

As described above, LiPF$_6$ having high ion conductivity and wide potential window is an essential electrolyte to exhibit good battery performance, but has a problem of thermal stability. Even when a specific phosphorous acid ester or hexamethylphosphoramide proposed to solve the problems is added, acceptable battery performance cannot be obtained due to poor electrochemical stability.

CITATION LIST

Patent Literature

Patent Literature 1: JP2002-356491
Patent Literature 2: JP2003-34692
Patent Literature 3: WO2010/092829 Pamphlet
Patent Literature 4: Specification of U.S. Pat. No. 6,939,647
Patent Literature 5: JP2011-3498

Non-Patent Literature

Non-Patent Literature 1: Masashi Ishikawa supervising ed., CMC Publishing Co., LTD., "Technologies and Materials for Lithium Ion Capacitor," issued on Oct. 21, 2010
Non-Patent Literature 2: Hideo Tamura supervising ed., NTS Inc., "Functional Chemistry of Electrons and Ions, Series vol. 3, Lithium Ion Secondary Battery of Next Generation Type," issued on May 26, 2003
Non-Patent Literature 3: Kunitaka Momota, "Battery Technology," vol. 8, (1996), p. 108
Non-Patent Literature 4: Journal of Power Sources, vol. 113, (2003), p. 166
Non-Patent Literature 5: Journal of The Electrochemical Society, vol. 152, (2005), p. A1361

SUMMARY OF INVENTION

Technical Problem

As a decomposition mechanism of LiPF$_6$ by heat, a mechanism shown by the formula (II) is known as described in Non-Patent Literature 5, or the like.

[Chemical Formula 1]

LiPF$_6$ is dissociated into LiF and PF$_5$ by heating. Since PF$_5$ produced by dissociation is very unstable, a mechanism in which decomposition is promoted by a trace amount of water content in an electrolyte solution, like the formula (III), or PF$_5$ reacts with a solvent in the electrolyte solution resulting in decomposition is considered. Since HF produced at this time further promotes decomposition of LiPF$_6$, the battery performance is rapidly reduced.

[Chemical Formula 2]

For stabilization of unstable PF$_5$, use of a phosphoric acid ester or hexamethylphosphoramide is known. However, since these compounds have low electrochemical stability, the compounds are subjected to a side reaction on an electrode in a nonaqueous secondary battery, and especially a lithium secondary battery. Thus, not only an effect of stabilizing PF$_5$ is reduced, but also the internal resistance in the battery increases, and this deteriorates the battery.

The present invention has been made in view of these problems. An object of the present invention is to provide a method for stabilizing a solution that contains LiPF$_6$ by increasing thermal stability of LiPF$_6$ without changing the structure thereof and also to provide an electrolyte solution for nonaqueous secondary batteries that contains LIPF$_6$ thermally and electrochemically stabilized.

Solution to Problem

The present inventors have intensively investigated to solve the problems. As a result, the present inventors have found that when a phosphoric acid ester amide having a specific structure is allowed to coexist in a solution containing LiPF$_6$, the thermal stability of LiPF$_6$ is improved, and when the stabilized LiPF$^6$-containing solution is used, a nonaqueous electrolyte solution that has high ion conductivity and a performance maintained over a long period can be obtained. Thus, the present invention has been completed. Specifically, the present invention includes the following outlines.

(1) A method for stabilizing LiPF$_6$, comprising making a phosphoric acid ester amide represented by the following general formula (I) coexist with LiPF$_6$ in a solution containing LiPF$_6$:

[Chemical Formula 3]

(I)

(in the formula, m represents an integer of 1 or 2; each of R$^1$ and R$^2$ represents a branched or linear alkyl group having 1 to 6 carbon atoms and/or a hydrocarbon group having an unsaturated bond, provided that R$^1$ and R$^2$ may have a substituent that is selected from the group consisting of an alkoxy group, an amino group, an alkylthio group, a saturated heterocyclic group, an unsaturated heterocyclic group, and a fluorine atom, and R$^1$ and R$^2$ may combine together to form a 5 to 8 membered cyclic structure; and R$^3$ represents a branched or linear alkyl group having 1 to 6 carbon atoms or a branched or linear fluorine-containing alkyl group having 1 to 6 carbon atoms).

As shown in the above general formula (I), it is necessary that the phosphoric acid ester amide have an amido group and an ester group in one molecule in the method of the present invention. An amido group has an effect of stabilizing LiPF$_6$, and an amido group alone is likely to be oxidized. Therefore, when an amido group and an ester group are present in the molecule, electrochemical stability is improved.

On the other hand, a method using a fluorine-containing phosphoric acid ester amide as a solvent of an electrolyte solution has been proposed (JP2011-141974). The fluorine-containing phosphoric acid ester amide shown in the prior art is used mainly for the purpose of imparting flame retardance and self-extinction property to the electrolyte solution. In order to achieve the purpose, a fluorine atom is necessary, and it is necessary that a substantially effective amount added to the electrolyte solution be as large as 20% by weight or more with respect to the amount of the electrolyte solution. This literature also describes that charge and discharge characteristics at low temperature and high rate charge and discharge characteristics are improved as compared with a conventional flame retardant, but does not disclose the investigation of thermal stability of a nonaqueous electrolyte solution using LiPF$_6$, and does not mention a stabilization effect thereof.

The present invention is characterized by adding a phosphoric acid ester amide for the purpose of stabilizing LiPF$_6$. The present invention exhibits an effect even when a fluorine atom is not included in the phosphoric acid ester amide and the molar ratio of the phosphoric acid ester amide with respect to LiPF$_6$ is substantially as small as 0.001 (for example, about 0.014% by weight with respect to an electrolyte solution in Example 13 of the present invention). Therefore, the present invention has a concept quite different from the prior art.

Thus, when the phosphoric acid ester has both an amido group and an ester group in the molecule, both the thermal stabilization effect of LiPF$_6$ and the oxidation resistance of LiPF$_6$ in the nonaqueous electrolyte solution are achieved. This is a surprising effect, and is unlikely to be presumed by a person skilled in the art with ease.

(2) In the above general formula (I), the oxidation resistance is improved by the combination of one amido group and two ester groups, and the oxidation resistance is further improved by converting a substituent bonded to the ester group into a fluorine-containing alkyl group.

(3) Herein, it is necessary that the solution containing LiPF$_6$ contain the phosphoric acid ester amide represented by the above general formula (I) in such an amount that the molar ratio of the phosphoric acid ester amide with respect to LiPF$_6$ is 0.001 to 2. When the amount of the phosphoric acid ester amide with respect to LiPF$_6$ is less than the lower limit, the effect obtained by addition is low. When it is more than the upper limit, the solubility of LiPF$_6$ and the ion conductivity may decrease.

(4) The present invention relates to the method for stabilizing LiPF$_6$ described in any one of (1) to (3), wherein the solution containing LiPF$_6$ contains a cyclic carbonate and/or a chain carbonate as a solvent.

(5) A nonaqueous electrolyte solution for nonaqueous secondary batteries that has increased thermal and storage stabilities, containing LiPF$_6$ as an electrolyte and a cyclic carbonate and/or a chain carbonate as a solvent, and a phosphoric acid ester amide represented by the following general formula (I) in such an amount that the molar ratio of the phosphoric acid ester amide with respect to $LiPF_6$ is 0.001 to 2:

[Chemical Formula 4]

(I)

(in the formula, m represents an integer of 1 or 2; each of $R^1$ and $R^2$ represents a branched or linear alkyl group having 1 to 6 carbon atoms and/or a hydrocarbon group having an unsaturated bond, provided that $R^1$ and $R^2$ may have a substituent that is selected from the group consisting of an alkoxy group, an amino group, an alkylthio group, a saturated heterocyclic group, an unsaturated heterocyclic group, and a fluorine atom, and $R^1$ and $R^2$ may combine together to form a 5 to 8 membered cyclic structure; and $R^3$ represents a branched or linear alkyl group having 1 to 6 carbon atoms or a branched or linear fluorine-containing alkyl group having 1 to 6 carbon atoms).

(6) A nonaqueous electrolyte solution for nonaqueous secondary batteries that has increased thermal and storage stabilities under a condition at a high temperature of 30 to 100° C., contains $LiPF_6$ as an electrolyte and a cyclic carbonate and/or a chain carbonate as a solvent, and contains a phosphoric acid ester amide represented by the following general formula (I) in such an amount that the molar ratio of the phosphoric acid ester amide with respect to $LiPF_6$ is 0.001 to 2:

[Chemical Formula 5]

(I)

(in the formula, m represents an integer of 1 or 2; each of $R^1$ and $R^2$ represents a branched or linear alkyl group having 1 to 6 carbon atoms and/or a hydrocarbon group having an unsaturated bond, provided that $R^1$ and $R^2$ may have a substituent that is selected from the group consisting of an alkoxy group, an amino group, an alkylthio group, a saturated heterocyclic group, an unsaturated heterocyclic group, and a fluorine atom, and $R^1$ and $R^2$ may combine together to form a 5 to 8 membered cyclic structure; and $R^3$ represents a branched or linear alkyl group having 1 to 6 carbon atoms or a branched or linear fluorine-containing alkyl group having 1 to 6 carbon atoms).

(7) A nonaqueous secondary battery that has increased thermal and storage stabilities, including a positive electrode and a negative electrode that are capable of occluding and releasing lithium, a separator, and an electrolyte solution that contains $LiPF_6$ as an electrolyte and a cyclic carbonate and/or a chain carbonate as a solvent, and contains a phosphoric acid ester amide represented by the following general formula (I) in such an amount that the molar ratio of the phosphoric acid ester amide with respect to $LiPF_6$ is 0.001 to 2:

[Chemical Formula 6]

(in the formula, m represents an integer of 1 or 2; each of $R^1$ and $R^2$ represents a branched or linear alkyl group having 1 to 6 carbon atoms and/or a hydrocarbon group having an unsaturated bond, provided that $R^1$ and $R^2$ may have a substituent that is selected from the group consisting of an alkoxy group, an amino group, an alkylthio group, a saturated heterocyclic group, an unsaturated heterocyclic group, and a fluorine atom, and $R^1$ and $R^2$ may combine together to form a 5 to 8 membered cyclic structure; and $R^3$ represents a branched or linear alkyl group having 1 to 6 carbon atoms or a branched or linear fluorine-containing alkyl group having 1 to 6 carbon atoms).

(8) A lithium ion capacitor that has increased thermal and storage stabilities, including a second electrode that is disposed so as to be opposite to a first electrode capable of reversibly supporting lithium ions, a separation membrane disposed between the first and second electrodes, and an electrolyte solution that contains $LiPF_6$ as an electrolyte and a cyclic carbonate and/or a chain carbonate as a solvent, and contains a phosphoric acid ester amide represented by the following general formula (I) in such an amount that the molar ratio of the phosphoric acid ester amide with respect to $LiPF_6$ is 0.001 to 2:

[Chemical Formula 7]

(in the formula, m represents an integer of 1 or 2; each of $R^1$ and $R^2$ represents a branched or linear alkyl group having 1 to 6 carbon atoms and/or a hydrocarbon group having an unsaturated bond, provided that $R^1$ and $R^2$ may have a substituent that is selected from the group consisting of an alkoxy group, an amino group, an alkylthio group, a saturated heterocyclic group, an unsaturated heterocyclic group, and a fluorine atom, and $R^1$ and $R^2$ may combine together to form a 5 to 8 membered cyclic structure; and $R^3$ represents a branched or linear alkyl group having 1 to 6 carbon atoms or a branched or linear fluorine-containing alkyl group having 1 to 6 carbon atoms).

Advantageous Effects of Invention

The present invention provides a method for stabilizing a solution that contains $LiPF_6$ by increasing thermal stability of $LiPF_6$ without changing the structure of $LiPF_6$, an electrolyte solution for nonaqueous secondary batteries that contains $LIPF_6$ stabilized at high temperature, and a nonaqueous secondary battery that is stable at high temperature.

DESCRIPTION OF EMBODIMENTS

The present inventors have found that when a solution containing $LiPF_6$ contains a phosphoric acid ester amide represented by the general formula (I), both stabilization of $LiPF_6$ and improvement of oxidation resistance of $LiPF_6$ can be achieved. The present invention has thereby been completed. Hereinafter, embodiments according to the present invention will be described in detail.

In the general formula (I), m represents an integer of 1 or 2. Since the phosphoric acid ester amide has both an amido group and an ester group in the molecule, both the thermal stabilization effect of $LiPF_6$ and the oxidation resistance of $LiPF_6$ in the nonaqueous electrolyte solution can be achieved. As also described in Solution To Problem, an amido group alone can stabilize $LiPF_6$, but that including only an amido group is electrochemically unstable inside a battery, and an ester group alone does not have a sufficient stabilization effect of $LiPF_6$.

As described above, JP 2011-141074 proposes a method for adding a fluorine-containing phosphoric acid ester to an electrolyte solution to improve flame retardance of a non-aqueous electrolyte solution, and simply describes suppression of combustion of a combustible solvent and improvement of charge and discharge characteristics at low temperature and effective charge and discharge characteristics as effects. These effects are different from the effects found in the present invention, in which both high oxidation resistance and the stabilization effect of $LiPF_6$ are achieved.

In the general formula (I), each of $R^1$ and $R^2$ independently represents a branched or linear alkyl group having 1 to 6 carbon atoms and/or a hydrocarbon group having an unsaturated bond, provided that $R^1$ and $R^2$ may have a substituent that is selected from the group consisting of an alkoxy group, an amino group, an alkylthio group, a saturated heterocyclic group, an unsaturated heterocyclic group, and a fluorine atom, and $R^1$ and $R^2$ may combine together to form a 5 to 8 membered cyclic structure.

In the general formula (I), specific examples of $R^1$ and $R^2$ may include a methyl group, an ethyl group, a n-propyl group, an isopropyl group, a n-butyl group, an isobutyl group, a sec-butyl group, a tert-butyl group, a n-amyl group, a tert-amyl group, a 3-cyclopentyl group, a n-hexyl group, a cyclohexyl group, a 2-methoxyethyl group, a 2-ethoxyethyl group, a trifluoromethyl group, a 2,2,2-trifluoroethyl group, a 2,2-difluoroethyl group, a 2,2,3,3-tetrafluoropropyl group, a 2,2,3,3,3-pentafluoropropyl group, a 2-(piperidin-1-yl) ethyl group, a 2-(piperazin-1-yl)ethyl group, a 2-(N'-methylpiperazin-1-yl]ethyl group, a 2-(morpholin-1-yl)ethyl group, a 2-(pyrrol-1-yl)ethyl group, a 2-aminoethyl group, a 2-methylaminoethyl group, a 2-dimethylaminoethyl group, a 2-methylthioethyl group, and a 2-ethylthioethyl group. Among these, a methyl group, an ethyl group, a n-propyl group, and an isopropyl group are preferred since raw materials for them are industrially available with ease.

In the general formula (I), specific examples of $R^1$ and $R^2$ having an unsaturated bond may include an allyl group, a 2-butenyl group, a 3-butenyl group, a 2-propenyl group, a 2-propynyl group, a phenyl group a naphthyl group, a benzyl group, a tolyl group, a mesityl group, a 2-cyclohexenyl group, a 2-(imidazol-1-yl)ethyl group, and a 2-(2-methyl-imidazol-1-yl)ethyl group. Substituents of these are known to be electrochemically unstable, but form an ion transmissive film by an electrochemical action, and the stabilization effect of $LiPF_6$ may be maintained.

In the general formula (I), $R^3$ represents a branched or linear alkyl group having 1 to 6 carbon atoms or a branched or linear fluorine-containing alkyl group having 1 to 6 carbon atoms. Examples of the linear or branched alkyl group having 1 to 6 carbon atoms may include a methyl group, an ethyl group, a n-propyl group, an isopropyl group, a n-butyl group, an isobutyl group, a sec-butyl group, a tert-butyl group, a n-amyl group, a tert-amyl group, a n-hexyl group, and a cyclohexyl group. Examples of the linear or branched fluorine-containing alkyl group having 1 to 6 carbon atoms may include a trifluoromethyl group, a 2,2,2-trifluoroethyl group, a 2,2-difluoroethyl group, a 2-fluoroethyl group, a perfluoroethyl group, a 2,2,3,3-tetrafluoropropyl group, a 2,2,3,3,3-pentafluoropropyl group, a 1,1,2,2,3,3,4,4-octafluorobutyl group, a perfluorobutyl group, a 2,2,3,3,4,4,5,5-octafluoropentyl group, a perfluoropentyl group, and a 3,3,4,4,5,5,6,6-nonafluorohexyl group. It is preferable that at least one of $R^3$s is a fluorine-containing alkyl group. Of the fluorine-containing alkyl groups, a 2,2-difluoroethyl group, a 2,2,2-trifluoroethyl group, a 2,2,3,3-tetrafluoropropyl group, and a 2,2,3,3,3-pentafluoropropyl group are particularly preferred in terms of physical properties of an electrolyte solution and oxidation resistance.

Specific examples of the phosphoric acid ester amide represented by the general formula (I) may include N,N-dimethylamide dimethyl phosphate, N,N-dimethylamide diethyl phosphate, N,N-diethylamide dimethyl phosphate, N,N-diethylamide diethyl phosphate, N,N-di-n-propylamide dimethyl phosphate, N,N-di-n-propylamide diethyl phosphate, N,N-diisopropylamide dimethyl phosphate, N,N-diisopropylamide diethyl phosphate, N,N-dimethylamide bis (2,2,2-trifluoroethyl)phosphate, N,N-diethylamide bis(2,2,2-trifluoroethyl)phosphate, N,N-di-n-propylamide bis(2,2,2-trifluoroethyl)phosphate, N,N-diisopropylamide bis(2,2,2-trifluoroethyl)phosphate, N,N-di-n-butylamide bis(2,2,2-trifluoroethyl)phosphate, N,N-diisobutylamide bis(2,2,2-trifluoroethyl)phosphate, N,N-di-sec-butylamide bis(2,2,2-trifluoroethyl)phosphate, N,N-di-tert-butylamide bis(2,2,2-trifluoroethyl)phosphate, N,N-di-n-amylamide bis(2,2,2-trifluoroethyl)phosphate, N,N-dimethylamide bis(2,2-difluoroethyl)phosphate, N,N-diethylamide bis(2,2-difluoroethyl)phosphate, N,N-di-n-propylamide bis(2,2-difluoroethyl)phosphate, N,N-diisopropylamide bis(2,2-difluoroethyl)phosphate, N,N-di-n-butylamide bis(2,2-difluoroethyl)phosphate, N,N-diisobutylamide bis(2,2-difluoroethyl)phosphate, N,N-di-sec-butylamide bis(2,2-difluoroethyl)phosphate, N,N-di-tert-butylamide bis(2,2-difluoroethyl)phosphate, N,N-di-n-amylamide bis(2,2-difluoroethyl)phosphate, N,N-dimethylamide bis(2,2,3,3-tetrafluoropropyl)phosphate, N,N-diethylamide bis(2,2,3,3-tetrafluoropropyl)phosphate, N,N-di-n-propylamide bis(2,2,3,3-tetrafluoropropyl)phosphate, N,N-diisopropylamide bis (2,2,3,3-tetrafluoropropyl)phosphate, N,N-di-n-butylamide bis(2,2,3,3-tetrafluoropropyl)phosphate, N,N-diisobutylamide bis(2,2,3,3-tetrafluoropropyl)phosphate, N,N-di-sec-butylamide bis(2,2,3,3-tetrafluoropropyl)phosphate, N,N-di-tert-butylamide bis(2,2,3,3-tetrafluoropropyl)phosphate, N,N-di-n-amylamide bis(2,2,3,3-tetrafluoropropyl)phosphate, bis(N,N-dimethylamide) (2,2,2-trifluoroethyl)phosphate, bis(N,N-diethylamide) (2,2,2-trifluoroethyl)phosphate, bis(N,N-di-n-propylamide) (2,2,2-trifluoroethyl) phosphate, and bis(N,N-diisopropylamide) (2,2,2-trifluoroethyl)phosphate.

Examples of the phosphoric acid ester amide in which $R^1$ and $R^2$ combine together to form a 4 to 8 membered cyclic structure may include pyrrolidide bis(2,2,2-trifluoroethyl)phosphate, piperidide bis(2,2,2-trifluoroethyl)phosphate, morpholide bis(2,2,2-trifluoroethyl)phosphate, thiomorpholide bis(2,2,2-trifluoroethyl)phosphate, N'-methylpiperazide bis(2,2,2-trifluoroethyl)phosphate, N'-methylpiperazide bis(2,2,3,3-tetrafluoropropyl)phosphate, N'-methylpiperazide bis(2,2,3,3,3-pentafluoropropyl)phosphate, N'-methylpiperazide bis(2,2,3,3,4,4,5,5-octafluoropentyl)phosphate, N'-methylpiperazide bis(2,2,3,3,4,4,5,5,6,6,7,7-dodecafluoroheptyl)phosphate, N'-methylpiperazide bis(2,2,3,3,4,4,5,5,6,6,7,7-dodecafluoroheptyl)phosphate, and N'-methylpiperazide 2,2,3,3-tetrafluoropropyl 2,2,2-trifluoroethyl phosphate.

Among these phosphoric acid ester amides, one or more of N,N-dimethylamide bis(2,2-difluoroethyl)phosphate, N,N-diethylamide bis(2,2-difluoroethyl)phosphate, N,N-di-n-propylamide bis(2,2-difluoroethyl)phosphate, N,N-diisopropylamide bis(2,2-difluoroethyl)phosphate, N,N-dimethylamide bis(2,2,2-trifluoroethyl)phosphate, N,N-diethylamide bis(2,2,2-trifluoroethyl)phosphate, N,N-di-n-propylamide bis(2,2,2-trifluoroethyl)phosphate, N,N-diisopropylamide bis(2,2,2-trifluoroethyl)phosphate, N,N-dimethylamide bis(2,2,3,3-tetrafluoropropyl)phosphate, N,N-diethylamide bis(2,2,3,3-tetrafluoropropyl)phosphate, N,N-di-n-propylamide bis(2,2,3,3-tetrafluoropropyl)phosphate, and N,N-diisopropylamide bis(2,2,3,3-tetrafluoropropyl)phosphate, or a mixture thereof is preferably used.

The amount of phosphoric acid ester amide in the nonaqueous electrolyte solution in a molar ratio with respect to $LiPF_6$ is 0.001 to 2, preferably 0.001 to 1, and more preferably 0.001 to 0.76. When the amount of phosphoric acid ester amide is less than 0.001 with respect to $LiPF_6$, the stabilization effect of $LiPF_6$ is not sufficient. When it exceeds 2, the ion conductivity may decrease, or $LiPF_6$ may be deposited from the $LiPF_6$-containing solution.

It is preferable that an aprotic solvent be used as the solvent of the $LiPF_6$ solution of the present invention. Examples of the aprotonic solvent may include esters such as methyl acetate, ethyl acetate, butyl acetate, methyl propionate, ethyl propionate, and ethyl trifluoroacetate, ethers such as diisopropyl ether, tetrahydrofuran, dioxolane, dimethoxyethane, diethoxyethane, methoxyethoxyethane, (2,2,3,3-tetrafluoroethyl) 2,2,2-trifluoroethyl ether, and (2,2,3,3-tetrafluoroethyl) 2,2,3,3-tetrafluoropropyl ether, lactones such as γ-butyrolactone and γ-valerolactone, chain sulfones such as dimethylsulfone and diethylsulfone, cyclic sulfones such as sulfolane, chain carbonates such as dimethyl carbonate, diethyl carbonate, ethylmethyl carbonate, diphenyl carbonate, bis(2,2,2-trifluoroethyl)carbonate, and (2,2,2-trifluoroethyl)methyl carbonate, cyclic carbonates such as ethylene carbonate, propylene carbonate, butylene carbonate, chloroethylene carbonate, and fluoroethylene carbonate, and a mixture of two or more kinds thereof. Among these solvents, acyclic carbonate, a chain carbonate, or a mixture thereof is preferably used in terms of stability of $LiPF_6$. The amount of the aprotic solvent used in a weight ratio with respect to $LiPF_6$ is usually 1 to 10. In particular, when the $LiPF_6$ solution is used as a nonaqueous electrolyte solution for nonaqueous secondary batteries, it is desirable that the solution be used so that the concentration of $LiPF_6$ falls within a range of 0.5 to 1.5 mol/L.

In the present invention, a method for mixing $LiPF_6$ and a fluorine-containing phosphoric acid ester amide represented by the general formula (I) is not particularly limited, and examples thereof may include a method for adding a fluorine-containing phosphoric acid ester amide to $LiPF_6$, a method for adding $LiPF_6$ to a fluorine-containing phosphoric acid ester amide, a method for adding a mixed solvent of fluorine-containing phosphoric acid ester amide and another aprotic solvent to $LiPF_6$, a method for adding $LiPF_6$ to a mixed solvent of fluorine-containing phosphoric acid ester amide and another aprotic solvent, and a method for adding a fluorine-containing phosphoric acid ester amide to a solution of $LiPF_6$ in an aprotic solvent.

According to the method of the present invention, the thermal stability and storage stability of the $LiPF_6$-containing solution are enhanced. Therefore, the method of the present invention is useful for storage and transportation of $LiPF_6$ in the form of a solution.

The method of the present invention is particularly useful for use in the $LiPF_6$-containing solution as a nonaqueous electrolyte solution for nonaqueous secondary batteries such as a lithium ion secondary battery. When the method of the present application is applied to a nonaqueous electrolyte solution, the thermal stability of $LiPF_6$ is enhanced. Therefore, a battery can be used not only at a low temperature of lower than 30° C. but also at a high temperature of 30 to 100° C., and preferably 40 to 90° C., for a long time without a decrease in performance. Under such conditions, the ion conductivity of the nonaqueous electrolyte solution is increased, and excellent battery performance can be achieved.

The storage stability in the present invention means that $LiPF_6$ can be stably stored without degradation of performance by suppressing decomposition of $LiPF_6$ even under difficult temperature control such as at high temperature in summer and in the hot sun out of doors, although decomposition of $LiPF_6$ is so small as to be ignorable under general temperature control.

In the method of the present invention, even when the $LiPF_6$-containing solution is used as a nonaqueous electrolyte solution for nonaqueous secondary batteries such as a lithium ion secondary battery, it is preferable that a cyclic carbonate, a chain carbonate, or a mixture thereof be used in terms of battery performance If necessary, a film former such as vinylene carbonate may be added to the nonaqueous electrolyte solution.

Secondary batteries using $LiPF_6$ as an electrolyte are collectively referred to as the nonaqueous secondary battery of the present invention. Specific examples thereof may include a lithium secondary battery using metallic lithium, a lithium ion secondary battery, an electric double layer capacitor, and a lithium ion capacitor.

A lithium secondary battery or a lithium ion secondary battery of the present invention is composed of at least a positive electrode, a negative electrode, and a separator. As a positive electrode material, a composite oxide of a transition metal and lithium such as $LiCoO_2$, $LiNiO_2$, $LiMn_2O_4$, $LiNi_{1/3}Co_{1/3}Mn_{1/3}O_2$, $LiNi_{1/4}Mn_{3/4}O_4$, $LiFeO_2$, and $LiFePO_4$ is usually used.

As a negative electrode material, metallic lithium, a lithium alloy, or a carbon material capable of doping or dedoping lithium ions, or a composite oxide such as lithium titanate is used.

As the separator, a micro porous film or the like is used. As a material, a polyolefin-based resin such as polyethylene or a fluorinated resin such as polyvinylidene fluoride is used.

An electric double layer capacitor or lithium ion capacitor of the present invention is composed of at least a positive electrode, a negative electrode, and a separator. As a positive electrode material, a substance capable of reversibly supporting lithium ions is used. Examples thereof may include activated carbon, a conductive macromolecule, and a polyacene-based substance (PAS) that is a heat-treated aromatic condensed polymer.

As a negative electrode material, a carbon material such as graphite capable of doping or dedoping lithium ions, and non-graphitizing carbon, a composite oxide such as lithium titanate, or PAS also exemplified as the positive electrode material is used.

As the separator, paper or non-woven fabric made of glass fibers is used.

A shape or form of the nonaqueous secondary battery is usually selected from a cylindrical form, a rectangular form, a coin form, a card form, and a laminate form.

EXAMPLES

Hereinafter, the present invention will be described in detail by Examples, but the present invention is not limited to the Examples.

Production Example 1

Production of Coin Cell-Type Lithium Secondary Battery

Lithium cobalt oxide ($LiCoO_2$) was used as a positive electrode active material, and carbon black as a conductive auxiliary agent and polyvinylidene fluoride (PVDF) as a binder were mixed thereto so that the weight ratio of $LiCoO_2$:carbon black:PVDF was 85:7:8. 1-Methyl-2-pyrrolidone was used to convert the mixture into a slurry. The slurry was applied to an aluminum collector at a given thickness, and dried to obtain a positive electrode.

Natural spherical graphite as a negative electrode active material and PVDF as a binder were mixed so that the weight ratio of graphite:PVDF was 9:1. 1-Methyl-2-pyrrolidone was used to convert the mixture into a slurry. The slurry was applied to a copper collector at a given thickness, and dried to obtain a negative electrode.

As a separator, an inorganic filler-containing polyolefin porous film was used.

Figure 1:
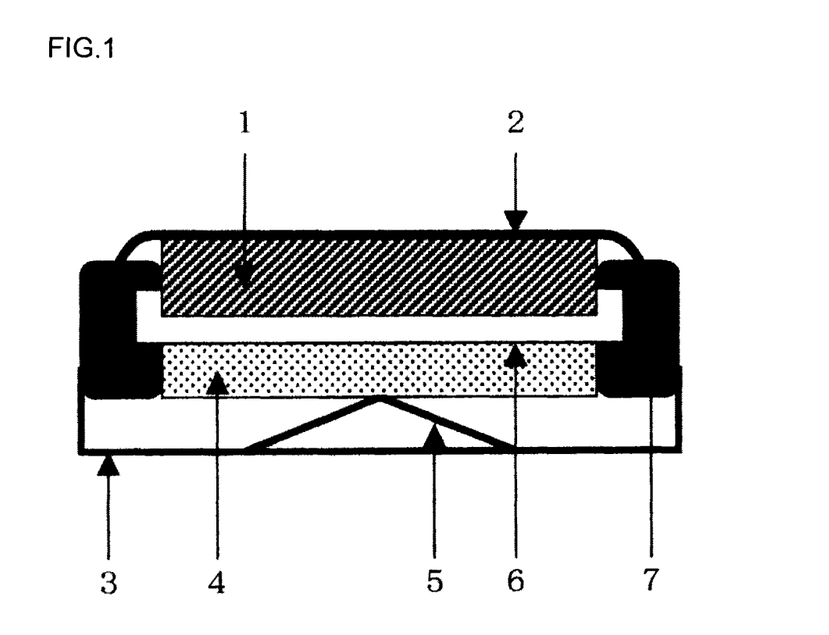
FIG. 1 shows a schematic cross-sectional view of a coin type lithium ion secondary battery in Examples 20 to 30 and Comparative Examples 7 to 12.

From the components, a lithium secondary battery using a coin type cell structure shown in FIG. 1 was produced. In the lithium secondary battery, a positive electrode 1 and a negative electrode 4 were disposed so as to be opposite to each other through a separator 6, and a layered body of the positive electrode 1, the separator 6, and the negative electrode 4 was set in a gasket 7. To this gasket 7, a positive electrode stainless-steel cap 2 and a negative electrode stainless-steel cap 3 were attached, and the positive electrode 1 constituting the layered body was pressed on the inside of the positive electrode stainless-steel cap 2 by a stainless-steel spring 5 provided in the negative electrode stainless-steel cap 3. Thus, a coin cell-type lithium ion secondary battery was produced.

Example 1

In a glove box of which inside air was replaced with argon, 3.8 g (25 mmol) of $LiPF_6$ and 1.6 g (4.6 mmol) of N,N-diisopropylamide bis(2,2,2-trifluoroethyl)phosphate were placed in a 25-mL measuring flask, and dissolved in a solvent obtained by mixing ethylene carbonate (hereinafter abbreviated as EC) and ethylmethyl carbonate (hereinafter abbreviated as EMC) at a volume ratio of 3 to 7 to a volume of 25 mL, to prepare a 1 mol/L $LiPF_6$ solution.

The resulting solution was colorless and transparent. The ion conductivity of the solution was measured at 25° C. using an ion conductivity measurement device (CM-117, manufactured by Kyoto Electronics Manufacturing Co., Ltd.) to be 8.38 mS/cm. The integral ratio of the peak of a decomposed substance of $LiPF_6$ to that of $LiPF_6$, which were observed by $^{19}$F-NMR (manufactured by BRUKER, 400 MHz) using deuterated acetone solvent (internal standard substance: trifluoromethyl benzene), was less than 0.1%.

Subsequently, this solution was placed in a closed vessel made of glass, and heated at 80° C. for 600 hours. After heating, the solution became pale yellow. The ion conductivity thereof was measured at 25° C. to be 8.38 mS/cm. The retention ratio of the ion conductivity was 100%. The integral ratio of the peak of a decomposed substance of $LiPF_6$ measured by $^{19}$F-NMR to the total peak of $LiPF_6$ and the decomposed substance was 0.12%. The results are shown in Table 1.

Comparative Example 1

A 1 mol/L $LiPF_6$ solution was prepared by the same operation as in Example 1 except that N,N-diisopropylamide bis(2,2,2-trifluoroethyl)phosphate was not used. The resulting solution was colorless and transparent. The ion conductivity of the solution was measured at 25° C. by an ion conductivity measurement device to be 9.26 mS/cm. The integral ratio of the peak of a decomposed substance of $LiPF_6$ measured by $^{19}$F-NMR to that of $LiPF_6$ was less than 0.1%.

This solution was then heated at 85° C. for 600 hours in the same manner as in Example 1, to obtain a dark-brown liquid. The ion conductivity thereof was measured at 25° C. to be 7.96 mS/cm. The retention ratio of the ion conductivity was 86%. The integral ratio of the peak of a decomposed substance of $LiPF_6$ measured by $^{19}$F-NMR to that of $LiPF_6$ was 12.8%. The results are shown in Table 1.

Examples 2 to 19 and Comparative Examples 2 to 6

In Examples 2 to 19 and Comparative Examples 2 to 6, a 1 mol/L $LiPF_6$ solution was prepared by the same operation as in Example 1.

Tables 1 and 2 show the amount of $LiPF_6$ used, the kind and the amount of phosphoric acid ester amide used, the ion conductivity before and after heating, the retention ratio of the ion conductivity, and the decomposition ratio of $LiPF_6$ determined by $^{19}$F-NMR in Examples 2 to 18 and Comparative Examples 2 to 6.

TABLE 1

| | LiPF₆ ADDITION AMOUNT mmol | ADDITIVE KIND | ADDITIVE ADDITION AMOUNT mmol | ADDITIVE/LiPF₆ MOLAR RATIO | ION CONDUCTIVITY INITIAL STAGE mS/cm | ION CONDUCTIVITY AFTER HEATING mS/cm | RETENTION RATIO % | LiPF₆ DECOMPOSITION RATIO % |
|---|---|---|---|---|---|---|---|---|
| EXAMPLE 1 | 25 | (iPr)₂N–P(=O)(OCH₂CF₃)₂ | 4.6 | 0.184 | 8.38 | 8.38 | 100 | 0.12 |
| EXAMPLE 2 | 25 | (Et)₂N–P(=O)(OCH₂CF₃)₂ | 5.1 | 0.204 | 8.59 | 8.59 | 100 | 0.12 |
| EXAMPLE 3 | 25 | (Me)₂N–P(=O)(OCH₂CF₃)₂ | 6.1 | 0.244 | 8.38 | 8.33 | 99.4 | 0.28 |
| EXAMPLE 4 | 25 | (Et)₂N–P(=O)(OCH₂CF₃)(N(Et)₂) | 6.0 | 0.240 | 8.35 | 8.27 | 99.0 | 0.32 |
| EXAMPLE 5 | 25 | (Me)₂N–P(=O)(OCH₂CH₃)₂ | 6.7 | 0.268 | 8.37 | 8.31 | 99.3 | 0.30 |
| EXAMPLE 6 | 25 | (iPr)₂N–P(=O)(OCH₂CF₃)₂ | 27.6 | 1.104 | 4.25 | 4.21 | 99.1 | 0.12 |
| EXAMPLE 7 | 25 | (iPr)₂N–P(=O)(OCH₂CF₃)₂ | 0.9 | 0.036 | 9.05 | 9.02 | 99.7 | 0.16 |
| EXAMPLE 8 | 25 | (iPr)₂N–P(=O)(OCH₂CF₃)₂ | 0.09 | 0.0036 | 9.10 | 9.06 | 99.6 | 0.22 |
| EXAMPLE 9 | 25 | 4-methylpiperazin-1-yl–P(=O)(OCH₂CF₂CF₂H)₂ | 4.8 | 0.192 | 8.41 | 8.40 | 99.9 | 0.13 |
| COMPARATIVE EXAMPLE 1 | 25 | — | — | — | 9.26 | 7.96 | 86.0 | 12.8 |

TABLE 1-continued

| | LiPF₆ ADDITION AMOUNT mmol | ADDITIVE KIND | ADDITIVE ADDITION AMOUNT mmol | ADDITIVE/ LiPF₆ MOLAR RATIO | ION CONDUCTIVITY INITIAL STAGE mS/cm | ION CONDUCTIVITY AFTER HEATING mS/cm | RETENTION RATIO % | LiPF₆ DECOMPOSITION RATIO % |
|---|---|---|---|---|---|---|---|---|
| COMPARATIVE EXAMPLE 2 | 25 |  | 30.5 | 1.220 | 7.85 | 6.91 | 88.0 | 2.80 |
| COMPARATIVE EXAMPLE 3 | 25 |  | 5.0 | 0.200 | 9.05 | 7.87 | 87.0 | 10.5 |
| COMPARATIVE EXAMPLE 4 | 25 |  | 26.5 | 1.060 | 3.86 | 3.74 | 96.9 | 1.32 |
| COMPARATIVE EXAMPLE 5 | 25 |  | 5.0 | 0.200 | 8.62 | 8.53 | 99.0 | 0.18 |
| COMPARATIVE EXAMPLE 6 | 25 |  | 5.0 | 0.200 | 9.02 | 8.99 | 99.7 | 0.21 |

TABLE 2

| | LiPF₆ ADDITION AMOUNT mmol | ADDITIVE KIND | ADDITIVE ADDITION AMOUNT mmol | ADDITIVE/ LiPF₆ MOLAR RATIO | ION CONDUCTIVITY INITIAL STAGE mS/cm | ION CONDUCTIVITY AFTER HEATING mS/cm | RETENTION RATIO % | LiPF₆ DECOMPOSITION RATIO % |
|---|---|---|---|---|---|---|---|---|
| EXAMPLE 10 | 25 |  | 3.0 | 0.120 | 8.46 | 8.40 | 99.3 | 0.18 |
| EXAMPLE 11 | 25 |  | 3.5 | 0.140 | 8.80 | 8.80 | 100 | 0.10 |
| EXAMPLE 12 | 25 |  | 19 | 0.760 | 6.48 | 6.42 | 99.1 | 0.13 |

TABLE 2-continued

| | LiPF₆ ADDITION AMOUNT mmol | ADDITIVE KIND | ADDITIVE ADDITION AMOUNT mmol | ADDITIVE/ LiPF₆ MOLAR RATIO | ION CONDUCITIVITY INITIAL STAGE mS/cm | ION CONDUCITIVITY AFTER HEATING mS/cm | RETENTION RATIO % | LiPF₆ DECOMPOSITION RATIO % |
|---|---|---|---|---|---|---|---|---|
| EXAMPLE 13 | 25 | (iPr)₂N—P(=O)(OCH₂CH₃)₂ | 0.025 | 0.001 | 9.25 | 9.20 | 99.5 | 0.28 |
| EXAMPLE 14 | 25 | morpholino-P(=O)(OCH₂CF₃)₂ | 3.5 | 0.140 | 8.82 | 8.75 | 99.2 | 0.32 |
| EXAMPLE 15 | 25 | thiomorpholino-P(=O)(OCH₂CF₃)₂ | 3.5 | 0.140 | 8.80 | 8.68 | 98.6 | 0.37 |
| EXAMPLE 16 | 25 | (Me)(Ph)N—P(=O)(OCH₂CF₃)₂ | 3.5 | 0.140 | 8.80 | 8.60 | 97.7 | 2.02 |
| EXAMPLE 17 | 25 | (Me)(Ph)N—P(=O)(OCH₂CH₃)₂ | 3.5 | 0.140 | 8.81 | 8.38 | 95.1 | 3.62 |
| EXAMPLE 18 | 25 | (Me)(allyl)N—P(=O)(OCH₂CF₃)₂ | 3.5 | 0.140 | 8.86 | 8.76 | 98.9 | 2.95 |
| EXAMPLE 19 | 25 | (Me)(propargyl)N—P(=O)(OCH₂CH₃)₂ | 3.5 | 0.140 | 8.86 | 8.20 | 92.6 | 2.70 |

Example 20

Charge and Discharge Test at High Temperature

In a glove box of which inside air was replaced with argon, 3.8 g (25 mmol) of LiPF₆ and 1.7 g (5 mmol) of N,N-diisopropylamide bis(2,2,2-trifluoroethyl)phosphate were placed in a 25-mL measuring flask, and dissolved in a solvent obtained by mixing EC and EMC at a volume ratio of 3 to 7 to a volume of 25 mL, to prepare a 1 mol/L LiPF₆ solution. A coin cell-type lithium secondary battery was produced using this electrolyte solution by the method in Production Example 1. Under a constant temperature condition of 25° C., this battery was charged at a charge current of 0.1 C and an upper limit voltage of 4.2 V, and then discharged at a discharge current of 0.1 C to a voltage of 3.0V. Under a constant temperature condition of 65° C., this battery was charged at a constant current of 1 C and a constant voltage of 4.2 V, and then discharged at a constant discharge current of 1 C to a final voltage of 3.0 V. This operation was repeated 100 times. The ratio of a 100th discharge capacity to a first discharge capacity was calculated as a charge and discharge cycle retention ratio. As a result, the ratio of the 100th discharge capacity to the first discharge capacity was 76%. The results are shown in Table 3.

Comparative Example 7

A 1 mol/L LiPF₆ solution was prepared by the same operation as in Example 20 except that N,N-diisopropylamide bis(2,2,2-trifluoroethyl)phosphate was not used. Thus, a coin cell-type lithium secondary battery was produced. Under a constant temperature condition of 25° C., this battery was charged at a charge current of 0.1 C and an upper limit voltage of 4.2 V, and then discharged at a discharge current of 0.1 C to a voltage of 3.0 V. Under a constant temperature condition of 65° C., this battery was charged at a constant charge current of 1 C and a constant voltage of 4.2 V, and then discharged at a constant discharge current of 1 C to a final voltage of 3.0 V. This operation was repeated 100 times. The ratio of a 100th discharge capacity to a first discharge capacity was calculated as a charge and discharge cycle retention ratio. As a result, the ratio of the 100th discharge capacity to the first discharge capacity largely decreased to 15%. The results are shown in Table 3.

Examples 21 to 29 and Comparative Examples 8 to 11

In Examples 21 to 29 and Comparative Examples 8 to 11, a 1 mol/L $LiPF_6$ solution having a composition shown in Tables 3 and 4 was prepared by the same operation as in Example 21.

A coin cell-type lithium secondary battery was produced using this solution in accordance with the method in Production Example 1. Under a constant temperature condition of 25° C., this battery was charged at a charge current of 0.1 C and an upper limit voltage of 4.2 V, and then discharged at a discharge current of 0.1 C to a voltage of 3.0 V. Under a constant temperature condition of 65° C., this battery was further charged at a constant charge current of 1 C and a constant voltage of 4.2 V, and then discharged at a constant discharge current of 1 C to a final voltage of 3.0 V. This operation was repeated 100 times. The ratio of a 100th discharge capacity to a first discharge capacity was calculated as a charge and discharge cycle retention ratio. The results are shown in Tables 3 and 4.

TABLE 3

| | $LiPF_6$ ADDITION AMOUNT mmol | ADDITIVE KIND | ADDITIVE ADDITION AMOUNT mmol | ADDITIVE/$LiPF_6$ MOLAR RATIO | TEST TEMPERATURE ° C. | CHARGE AND DISCHARGE CYCLE RETENTION RATIO % |
|---|---|---|---|---|---|---|
| EXAMPLE 20 | 25 | (iPr)$_2$N—P(=O)(OCH$_2$CF$_3$)$_2$ | 5 | 0.200 | 65 | 76 |
| EXAMPLE 21 | 25 | (nPr)$_2$N—P(=O)(OCH$_2$CF$_3$)$_2$ | 5 | 0.200 | 65 | 75 |
| EXAMPLE 22 | 25 | (CH$_3$)$_2$N—P(=O)(OCH$_2$CF$_3$)$_2$ | 5 | 0.200 | 65 | 77 |
| EXAMPLE 23 | 25 | piperazinyl—P(=O)(OCH$_2$CF$_2$CF$_2$H)$_2$ | 5 | 0.200 | 65 | 76 |
| EXAMPLE 24 | 25 | (Et)$_2$N—P(=O)(OCH$_2$CF$_3$)(N(Et)$_2$) | 5 | 0.200 | 65 | 70 |
| COMPARATIVE EXAMPLE 7 | 25 | — | — | — | 65 | 15 |
| COMPARATIVE EXAMPLE 8 | 25 | $H_3CO$—P(=O)(OCH$_3$)$_2$ | 5 | 0.200 | 65 | 18 |
| COMPARATIVE EXAMPLE 9 | 25 | $F_3CH_2CO$—P(=O)(OCH$_2$CF$_3$)$_2$ | 5 | 0.200 | 65 | 50 |

TABLE 3-continued

| | LiPF₆ ADDITION AMOUNT mmol | ADDITIVE KIND | ADDITIVE ADDITION AMOUNT mmol | ADDITIVE/LiPF₆ MOLAR RATIO | TEST TEMPERATURE °C | CHARGE AND DISCHARGE CYCLE RETENTION RATIO % |
|---|---|---|---|---|---|---|
| COMPARATIVE EXAMPLE 10 | 25 | F₃CH₂CO—P(—OCH₂CF₃)(OCH₂CF₃)=O | 5 | 0.200 | 65 | 48 |
| COMPARATIVE EXAMPLE 11 | 25 | (Me₂N)₃P=O | 5 | 0.200 | 65 | 8 |

TABLE 4

| | LiPF₆ ADDITION AMOUNT mmol | ADDITIVE KIND | ADDITIVE ADDITION AMOUNT mmol | ADDITIVE/LiPF₆ MOLAR RATIO | TEST TEMPERATURE °C | CHARGE AND DISCHARGE CYCLE RETENTION RATIO % |
|---|---|---|---|---|---|---|
| EXAMPLE 25 | 25 | (iPr)₂N—P(=O)(OCH₂CF₃)₂ | 3.5 | 0.140 | 65 | 76 |
| EXAMPLE 26 | 25 | (iPr)₂N—P(=O)(OCH₂CF₃)₂ | 0.025 | 0.001 | 65 | 77 |
| EXAMPLE 27 | 25 | Me₂N—P(=O)(OCH₂CH₃)₂ | 0.025 | 0.001 | 65 | 78 |
| EXAMPLE 28 | 25 | (Me)(Ph)N—P(=O)(OCH₂CF₃)₂ | 3.5 | 0.140 | 65 | 76 |
| EXAMPLE 29 | 25 | (Me)(allyl)N—P(=O)(OCH₂CF₃)₂ | 3.5 | 0.140 | 65 | 76 |

Production Example 2

Production of High-Voltage Lithium Secondary Battery

In a lithium-nickel-manganese complex oxide (LiNi$_{1/4}$Mn$_{3/4}$O$_4$) used as a positive electrode active material, acetylene black as a conductive auxiliary agent and polyvinylidene fluoride (PVDF) as a binder were mixed so that the weight ratio of LiNi$_{1/4}$Mn$_{3/4}$O$_4$:acetylene black:PVDF was 86:7:7. 1-Methyl-2-pyrrolidone was used to convert the mixture into a slurry. The slurry was applied to an aluminum collector at a given thickness, and dried to obtain a positive electrode. The same materials as those in Production Example 1 were used for components other than the positive electrode. Thus, a lithium secondary battery using a coin-type cell structure shown in FIG. 1 was produced.

Example 30

In a glove box of which inside air was replaced with argon, 3.8 g (25 mmol) of $LiPF_6$ and 1.7 g (5 mmol) of N,N-diisopropylamide bis(2,2,2-trifluoroethyl)phosphate were placed in a 25-mL measuring flask, and dissolved in a solvent obtained by mixing EC and EMC at a volume ratio of 3 to 7 to a volume of 25 mL, to prepare a 1 mol/L $LiPF_6$ solution. A coin cell-type lithium secondary battery was produced using this electrolyte solution by the method in Production Example 2. Under a constant temperature condition of 25° C., this battery was charged at a charge current of 0.1 C and an upper limit voltage of 4.8 V, and then discharged at a discharge current of 0.1 C to a voltage of 3.0 V. Under a constant temperature condition of 65° C., this battery was charged at a constant charge current of 1 C and a constant voltage of 4.8 V, and then discharged at a constant discharge current of 1 C to a final voltage of 3.0 V. This operation was repeated 100 times. The ratio of a 100th discharge capacity to a first discharge capacity was calculated as a charge and discharge cycle retention ratio. As a result, the ratio of the 100th discharge capacity to the first discharge capacity was 72%. The results are shown in Table 5.

Comparative Example 12

A 1 mol/L $LiPF_6$ solution was prepared by the same operation as in Example 30 except that N,N-diisopropylamide bis(2,2,2-trifluoroethyl)phosphate was not used. Thus, a coin cell-type lithium secondary battery was produced. Under a constant temperature condition of 25° C., this battery was charged at a charge current of 0.1 C and an upper limit voltage of 4.8 V, and then discharged at a discharge current of 0.1 C to a voltage of 3.0 V. Under a constant temperature condition of 65° C., this battery was charged at a constant current of 1 C and a constant voltage of 4.8 V, and then discharged at a constant discharge current of 1 C to a final voltage of 3.0 V. This operation was repeated 100 times. The ratio of a 100th discharge capacity to a first discharge capacity was calculated as a charge and discharge cycle retention ratio. As a result, the ratio of the 100th discharge capacity to the first discharge capacity decreased to 9%. The results are shown in Table 5.

Production Example 3

Production of Laminate-Type Lithium Ion Capacitor

An electrode using natural spherical graphite in Production Example 1 as an active material was used as a negative electrode. The negative electrode was impregnated in an electrolyte solution, and lithium ions were doped by an electrochemical doping method of applying current to a lithium foil as a counter electrode.

After the application of current, the voltage was gradually decreased. Lithium ions were then discharged from the lithium foil, and doped into the negative electrode.

Activated carbon commercially available as an active material for electric double layer capacitors was used for a positive electrode. In this activated carbon, carbon black as a conductive auxiliary agent, carboxymethyl cellulose (CMC) as a binder, and styrene-butadiene rubber (SBR) were mixed so that the weight ratio of activated carbon: carbon black:CMC:SBR was 80:10:5:5. The mixture was dispersed in water to obtain a slurry. The slurry was applied to an aluminum collector at a given thickness, and dried to obtain a positive electrode.

As a separator, an inorganic filler-containing polyolefin was used.

Figure 2:
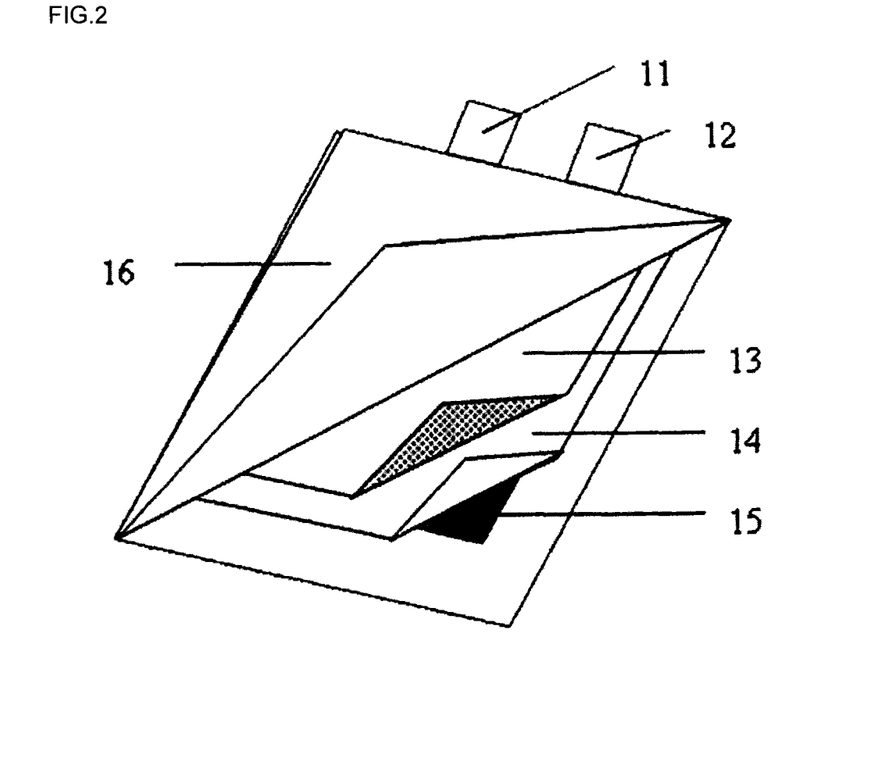
FIG. 2 shows a schematic cross-sectional view of a laminate type lithium ion capacitor in Example 31 and Comparative Example 13.

Using the components, a lithium ion capacitor structure shown in FIG. 2 was produced.

Example 31

High Temperature Test of Lithium Ion Capacitor

In a glove box of which inside air was replaced with argon, 3.8 g (25 mmol) of $LiPF_6$ and 1.7 g (5 mmol) of N,N-diisopropylamide bis(2,2,2-trifluoroethyl)phosphate were placed in a 25-mL measuring flask, and dissolved in a solvent obtained by mixing EC and EMC at a volume ratio of 3 to 7 to a volume of 25 mL, to prepare a 1 mol/L $LiPF_6$ solution. A laminate-type lithium ion capacitor was produced using this electrolyte solution by the method in Production Example 3.

This lithium ion capacitor was placed in a thermostatic oven at 65° C., a voltage of 3.8 V was applied for 500 hours, and the electrostatic capacity was measured. From measured values at the initial stage (0 hour) and after 500 hours, the electrostatic capacity retention ratio (%) and the internal resistance increasing ratio were calculated in accordance with the following equation.

TABLE 5

| | $LiPF_6$ ADDITION AMOUNT mmol | ADDITIVE KIND | ADDITION AMOUNT mmol | ADDITIVE/$LiPF_6$ MOLAR RATIO | TEST TEMPERATURE ° C. | CHARGE AND DISCHARGE CYCLE RETENTION RATIO % |
|---|---|---|---|---|---|---|
| EXAMPLE 30 | 25 |  | 5 | 0.200 | 65 | 72 |
| COMPARATIVE EXAMPLE 12 | 25 | — | — | — | 65 | 9 |

Electrostatic capacity retention ratio (%)=electrostatic capacity after 500 hours/electrostatic capacity at the initial stage×100

To measure the amount of gas generated in the high temperature test, the ratio of the cell volume after 500 hours to the laminate cell volume at the initial stage was calculated as a cell expansion ratio. The results are shown in Table 6.

Comparative Example 13

A 1 mol/L $LiPF_6$ solution was prepared by the same operation as in Example 31 except that N,N-diisopropylamide bis(2,2,2-trifluoroethyl)phosphate was not used. A laminate-type lithium ion capacitor was produced using this electrolyte solution by the method in Production Example 3.

The results of electrostatic capacity retention ratio (%) and cell expansion ratio (%) of this lithium ion capacitor at a temperature of 65° C. are shown in Table 6.

Example 6

Example 6 is an example in which the molar ratio of coexisting phosphoric acid ester amide to $LiPF_6$ was 1.104. In Example 6, the stabilization effect was the same as that in Example 1. However, the electrolyte solution viscosity increased, and the ion conductivity decreased to 50% or less as compared with the ion conductivity at the initial stage in Comparative Example 1 in which a phosphoric acid ester amide was not added.

Examples 11 to 13

Examples 11 to 13 are examples in which the molar ratios of coexisting phosphoric acid ester amide to $LiPF_6$ were 0.14, 0.76, and 0.001, respectively. The addition amounts at

TABLE 6

| | $LiPF_6$ ADDITION AMOUNT mmol | ADDITIVE KIND | ADDITIVE ADDITION AMOUNT mmol | ADDITIVE/ $LiPF_6$ MOLAR RATIO | TEST TEMPERATURE ° C. | ELECTROSTATIC CAPACITY INITIAL STAGE F | ELECTROSTATIC CAPACITY 500 h F | CAPACITY RETENTION RATIO % | CELL EXPANSION RATIO % |
|---|---|---|---|---|---|---|---|---|---|
| EXAMPLE 31 | 25 |  | 5 | 0.200 | 65 | 3.0 | 2.9 | 97 | 2 |
| COMPARATIVE EXAMPLE 13 | 25 | — | — | — | 65 | 3.1 | 2.7 | 88 | 213 |

Hereinafter, Examples and Comparative Examples of the present invention will be discussed.

Examples 1 to 19, and Comparative Example 1

It can be understood that all the $LiPF_6$-containing solutions stabilized by a phosphoric acid ester amide in accordance with the method of the present invention had higher ion conductivity retention ratio of ter heating and lower decomposition ratio of $LiPF_6$ as compared with the solution of Comparative Example 1 in which a phosphoric acid ester amide was not added. It is considered that $LiPF_6$ is decomposed into LiF and $PF_5$ and this further promotes decomposition, but decomposition of $LiPF_6$ was suppressed. This may be considered because the phosphoric acid ester amide of the present invention was interacted with $PF_5$ to stabilize $LiPF_6$ and suppress the decomposition.

Examples 1 to 19, and Comparative Examples 5 and 6

Comparative Examples 5 and 6 are examples in which tris(2,2,2-trifluoroethyl)phosphite as one kind of fluorine-containing phosphorous acid ester and hexamethylphosphoramide were added, respectively. As shown from the results, the fluorine-containing phosphorous acid ester and hexamethylphosphoramide had high stabilization effect of $LiPF_6$. Discussion of oxidation resistance will be given in Comparative Examples 10 and 11.

this time that are represented by a weight ratio to the electrolyte solution corresponded to 4%, 19%, and 0.014%, respectively.

As is clear from the results, even when the addition amount represented by a weight ratio of the phosphoric acid ester amide to the electrolyte solution was as very small as 0.014%, the stabilization effect at high temperature that is the object of the present invention could be exhibited. Further, it can be understood that this effect is different from that in the prior art (Japanese Patent Application Laid-Open No. 2011-141974).

In Example 12 in which a phosphoric acid ester amide was added in such an amount that the molar ratio was 0.76 with respect to $LiPF_6$ (the weight ratio was 19% with respect to the electrolyte solution), the ion conductivity at the initial stage was 70% as compared with Comparative Example 1 in which a phosphoric acid ester amide was not added, and was improved to a practical level of a battery.

In Example 11 in which a phosphoric acid ester amide was added in such an amount that the molar ratio was 0.14 with respect to $LiPF_6$ (the weight ratio was 4% with respect to the electrolyte solution), the ion conductivity was 95%, that is, an ion conductivity that substantially had no effect on battery performance could be obtained.

Examples 9, 14, and 15

Examples 9, 14, and 15 are examples of a phosphoric acid ester amide having a heterocyclic structure including, for example, nitrogen, oxygen, or sulfur. Even in the phosphoric acid ester amide having a heterocyclic structure, the stabilization effect of LiPF$_6$ was high.

Examples 20 to 23, and Comparative Example 7

In Example 20, N,N-diisopropylamide bis(2,2,2-trifluoroethyl)phosphate was allowed to coexist in a molar ratio of about 0.2 with respect to LiPF$_6$. Regardless of a high temperature condition of 65° C., high cycle retention ratio was maintained as compared with no addition in Comparative Example 6. This may be considered because deterioration of the electrolyte solution even inside the battery was suppressed by thermal stabilization of LiPF$_6$ as shown in Example 1. For N,N-diethylamide bis(2,2,2-trifluoroethyl) phosphate in Example 21, N,N-dimethylamide bis(2,2,2-trifluoroethyl)phosphate in Example 22, and N'-methylpiperazide bis(2,2,3,3-tetrafluoropropyl)phosphate in Example 23, it may be considered that good cycle characteristics were obtained by the same effect.

Example 24

Example 24 is an example in which bis(N,N-diethylamide) (2,2,2-trifluoroethyl)phosphate having one ester group and two amido groups in the molecule was added. In Example 24, the charge and discharge cycle characteristics were slightly lower as compared with Examples 20 to 23. This may be considered because the number of ester group in the phosphoric acid ester amide was the reason for a difference in oxidation resistance. Therefore, a phosphoric acid ester amide, especially a phosphoric acid ester amide having two ester groups may have high stabilization effect in charge and discharge at higher temperature.

Comparative Examples 8 to 11

Comparative Examples 8 and 9 are examples in which trimethyl phosphate containing no fluorine and tris(2,2,2-trifluoroethyl)phosphate that is a fluorine-containing phosphorous acid ester were added, respectively. It is considered that the phosphoric acid ester, and especially the fluorine-containing phosphoric acid ester have high oxidation resistance and they are stable in the electrolyte solution. However, since they have no amido group, the stabilization effect of LiPF$_6$ is low. Therefore, they may have decreased cycle characteristics as compared with the phosphoric acid ester amide of the present invention.

Comparative Examples 10 and 11 are examples in which tris(2,2,2-trifluoroethyl)phosphite and hexamethylphosphoramide, which have high thermal stabilization effect of LiPF$_6$, were added, respectively. In Comparative Examples 10 and 11, the cycle characteristics were low as compared with the phosphoric acid ester amide of the present invention. This may be considered because tris(2,2,2-trifluoroethyl)phosphite and hexamethylphosphoramide had low oxidation resistance as compared with the phosphoric acid ester amide of the present invention, the oxidation resistance of the additives themselves notably decreased due to repetition of charge and discharge at high temperature, the internal resistance increased due to deposition of decomposed substance on an electrode surface, or the like, and the battery performance was thus reduced.

Examples 16 to 19, 28, and 29

Examples 16 to 19, 28, and 29 are examples in each of which a phosphoric acid ester amide having an unsaturated hydrocarbon group that is bonded to an amido group, such as an alkyenyl group and an aryl group, was added. The stabilization effect of the phosphoric acid ester amide having an unsaturated hydrocarbon group in a high-temperature storage test was lower than that of a phosphoric acid ester amide having a saturated hydrocarbon group, and the battery performance of the former in the charge and discharge test at high temperature was the same as that of the latter. This may be because the stabilization effect in the liquid and the coating effect due to an electrochemical action acted synergistically.

Example 30 and Comparative Example 12

Example 30 and Comparative Example 12 are examples in which a LiNi$_{1/4}$Mn$_{3/4}$O$_4$ positive electrode that operates at higher voltage was used instead of the LiCoO$_2$ positive electrode. In a case of a general positive electrode that operates at high voltage, decomposition of an electrolyte solution and elution of metal in the positive electrode due to the decomposition are severe conditions for a battery. However, when the phosphoric acid ester amide of the present invention was allowed to coexist, an effect of suppressing a decrease in the battery performance was surprisingly seen. This cause is not clear, but it is considered that the phosphoric acid ester amide trapped PF$_5$ produced by decomposition of LiPF$_6$, and as a result, production of HF was suppressed, and decomposition of the solvent and elution of Ni and Mn were suppressed.

Example 31 and Comparative Example 13

Example 31 and Comparative Example 13 are examples using a lithium ion capacitor. Similarly to the lithium-ion secondary battery, it is considered that the thermal stability of the lithium ion capacitor was improved due to coexistence of the phosphoric acid ester amide of the present invention, and a decrease in the capacitor capacity and generation of gas due to decomposition were suppressed.

As described above, when a phosphoric acid ester amide of specific structure is allowed to coexist in a nonaqueous electrolyte solution containing LiPF$_6$, both stabilization of LiPF$_6$ and improvement of oxidation resistance can be achieved. These are surprising effects, and are unlikely to be presumed by a person skilled in the art with ease.

INDUSTRIAL APPLICABILITY

According to the method of the present invention, LiPF$_6$ can be stabilized at high temperature, and therefore this is useful for a nonaqueous electrolyte solution for nonaqueous secondary batteries.

REFERENCE SIGNS LIST

1: positive electrode
2: positive electrode stainless-steel cap
3: negative electrode stainless-steel cap
4: negative electrode
5: stainless-steel plate spring
6: inorganic filler-containing polyolefin porous separator
7: gasket
11: positive electrode lead
12: negative electrode lead
13: positive electrode
14: inorganic filler-containing polyolefin porous separator
15: negative electrode
16: laminate package

The invention claimed is:

1. A method for stabilizing LiPF$_6$, comprising mixing a phosphoric acid ester amide represented by the following general formula (I) with LiPF$_6$ in a solution comprising LiPF$_6$, in such an amount that a molar ratio of the phosphoric acid ester amide with respect to LiPF$_6$ is 0.001 to 2:

(I)

where:
m is 1 or 2;
each of R$^1$ and R$^2$ represents a branched or linear alkyl group comprising 1 to 6 carbon atoms and/or a hydrocarbon group comprising an unsaturated bond, wherein R$^1$ and R$^2$ optionally comprise a substituent that is selected from the group consisting of an alkoxy group, an amino group, an alkylthio group, a saturated heterocyclic group, an unsaturated heterocyclic group, and a fluorine atom, and wherein R$^1$ and R$^2$ optionally combine together to form a 5 to 8 membered cyclic structure; and
R$^3$ represents a branched or linear alkyl group comprising 1 to 6 carbon atoms or a branched or linear fluorine-containing alkyl group comprising 1 to 6 carbon atoms.

2. The method for stabilizing LiPF$_6$ according to claim 1, further comprising preparing the phosphoric acid ester amide.

(I)

3. The method for stabilizing LiPF$_6$ according to claim 1, wherein m is 1.

4. The method for stabilizing LiPF$_6$ according to claim 1, wherein R$^3$ is a fluorine-containing alkyl group.

5. The method for stabilizing LiPF$_6$ according to claim 1, wherein each of R$^1$ and R$^2$ independently represents a methyl group, an ethyl group, a n-propyl group or an isopropyl group, and R$^3$ represents a 2,2-difluoroethyl group, a 2,2,2-trifluoroethyl group, a 2,2,3,3-tetrafluoropropyl group or a 2,2,3,3,3-pentafluoropropyl group.

6. The method for stabilizing LiPF$_6$ according to claim 1, wherein the molar ratio of the phosphoric acid ester amide with respect to LiPF$_6$ is 0.001 to 1.

7. The method for stabilizing LiPF$_6$ according to claim 1, wherein the molar ratio of the phosphoric acid ester amide with respect to LiPF$_6$ is 0.001 to 0.76.

8. The method for stabilizing LiPF$_6$ according to claim 1, wherein the solution comprising LiPF$_6$ comprises a cyclic carbonate and/or a chain carbonate as a solvent.

9. A nonaqueous electrolyte solution comprising LiPF$_6$ as an electrolyte and a cyclic carbonate and/or a chain carbonate as a solvent, and a phosphoric acid ester amide represented by the following general formula (I) in such an amount that a molar ratio of the phosphoric acid ester amide with respect to LiPF$_6$ is 0.001 to 2:

(I)

where:
m is 1 or 2;
each of R$^1$ and R$^2$ represents a branched or linear alkyl group comprising 1 to 6 carbon atoms and/or a hydrocarbon group comprising an unsaturated bond, wherein R$^1$ and R$^2$ optionally comprise a substituent that is selected from the group consisting of an alkoxy group, an amino group, an alkylthio group, a saturated heterocyclic group, an unsaturated heterocyclic group, and a fluorine atom, and wherein R$^1$ and R$^2$ optionally combine together to form a 5 to 8 membered cyclic structure; and
R$^3$ represents a branched or linear alkyl group comprising 1 to 6 carbon atoms or a branched or linear fluorine-containing alkyl group comprising 1 to 6 carbon atoms.

10. The nonaqueous electrolyte solution according to claim 9, wherein the nonaqueous electrolyte solution has increased thermal and storage stabilities under a condition at a high temperature of 30 to 100° C.

(I)

11. A nonaqueous secondary battery comprising a positive electrode and a negative electrode that are capable of occluding and releasing lithium, a separator, an electrolyte solution comprising LiPF$_6$ as an electrolyte and a cyclic carbonate and/or a chain carbonate as a solvent and a phosphoric acid ester amide represented by the following general formula (I) in such an amount that a molar ratio of the phosphoric acid ester amide with respect to LiPF$_6$ is 0.001 to 2:

(I)

where:
m is 1 or 2;
each of R$^1$ and R$^2$ represents a branched or linear alkyl group comprising 1 to 6 carbon atoms and/or a hydrocarbon group comprising an unsaturated bond, wherein R$^1$ and R$^2$ optionally comprise a substituent that is selected from the group consisting of an alkoxy group, an amino group, an alkylthio group, a saturated heterocyclic group, an unsaturated heterocyclic group, and a fluorine atom, and wherein R$^1$ and R$^2$ optionally combine together to form a 5 to 8 membered cyclic structure; and
R$^3$ represents a branched or linear alkyl group comprising 1 to 6 carbon atoms or a branched or linear fluorine-containing alkyl group comprising 1 to 6 carbon atoms.

* * * * *